United States Patent [19]

Comparetto

[11] Patent Number: 4,632,102
[45] Date of Patent: Dec. 30, 1986

[54] BONE WEDGE OSTEOTOMY METHOD

[76] Inventor: John E. Comparetto, P.O. Box 433, Nassawadox, Va. 23413

[21] Appl. No.: 667,424

[22] Filed: Nov. 1, 1984

Related U.S. Application Data

[62] Division of Ser. No. 294,653, Aug. 20, 1981, Pat. No. 4,501,268.

[51] Int. Cl.⁴ .............................................. A61F 5/04
[52] U.S. Cl. ............................................. 128/92 VY
[58] Field of Search ............. 128/92 EB, 92 E, 92 H, 128/92 R, 92 XV, 92 XY, 92 X, 92 YJ

[56] References Cited

U.S. PATENT DOCUMENTS

| 2,737,724 | 3/1956 | Herz | 128/92 EB |
| 4,150,675 | 4/1979 | Comparetto | 128/92 E |
| 4,335,715 | 6/1982 | Kirkley | 128/92 EB |
| 4,501,268 | 2/1985 | Comparetto | 128/92 H |
| 4,509,511 | 4/1985 | Neufeld | 128/92 H |
| 4,565,191 | 1/1986 | Slocum | 128/92 EB |

Primary Examiner—Gene Mancene
Assistant Examiner—C. W. Shedd
Attorney, Agent, or Firm—Shoemaker and Mattare, Ltd.

[57] ABSTRACT

A wedge guide of specific angular dimensions allows the excision of a precise bone wedge by the alternate use of a crescentic and planar saw in a stable and accurate manner.

9 Claims, 18 Drawing Figures

BONE WEDGE OSTEOTOMY METHOD

This is a division of application Ser No. 294,653, filed Aug. 20, 1981, now U.S. Pat. No. 4,501,268.

THE BACKGROUND OF THE INVENTION

This patent application is being filed as a continuation in part of Ser. No. 127,010 Matrix Guide For A Precise Crescentric Wedge Ledge Osteotomy.

The wedge guide of this application allows the surgeon to make the surgical osteotomy invented by Comparetto and previously made with the cutting blade of U.S. Pat. No. 4,150,675, by more commonly used means ie. crescentic and planar saws. This present guide described herein is a preferred embodiment since it presents a more stable means for making the osteotomy. A still greater advantage is the less than 90° curved osteotomy with a slanted to the vertical planar section to thwart upward dorsal grade displacement of the healingly positioned bony parts of the osteotomy.

OBJECT OF THE INVENTION

An object of the invention is to provide a scalar means on the sides of the guide cylinder.

Another object of the invention is to provide a thicker more sturdy single tab means.

Another object of the invention is to provide individual degree guides. A still further object of the invention is to provide a stable wedge guide that has cylindrical and planar tab means that resist unwanted movement when making the planar cuts.

Another object of the invention is to provide a planar cutting guide that forms an acute angle with the curved cut.

A still further object of the invention is to provide a slanted from vertical planar cut that increases resistance to dislodgement of the healingly positioned bone parts. A still further object of the invention is to provide an adjustable planar tab means to yield varying wedge sizes for different degrees of correction.

A still further object of the invention is to provide multiple slot means for the placement of stabilizing tab means as well as cutting blades.

DETAILED DESCRIPTION OF THE INVENTION

Figure 1:
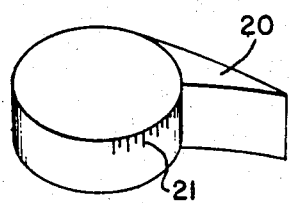
FIG. 1 is a perspective view of an embodiment of a guide that fits within or over a crescentic blade.

The original patent application shows a scale on the upper surface of the cylinder. Closely relating to this a scalar means can be placed on the wall of the cylinder. FIG. 1 shows a single tab means 20 to guide a planar cutting blade having a scalar means 21 on the cylinder wall. For purposes of tab means strength FIG. 1 also shows a thicker tab configuration than in the previous application.

Figure 1A:
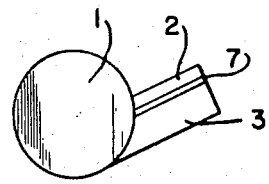
FIG. 1A is a view from above of an osteoguide.

The following descriptions relate to an improved embodiment of the first wedge guide. FIG. 1A is a view from above of the guide cylinder 1 which is of the same circumference as that of a matching crescentic blade. For example, an 18 mm crescentic blade forms a cut that would be an arc of an 18 mm guide cylinder. Off the cylinder's circumference is a degree block comprised of sections 2 and 3. Slot 7, FIG. 1A can be at any angle to a tangent T of the cylinder surface. In FIG. 1A it is depicted as less than 90°. Although the slot could be equal to, less than or greater than 90° the advantage of using an angulation of less than 90° is important because this will form a novel semi-curved Vee osteotomy that has greater stability.

Figure 2:
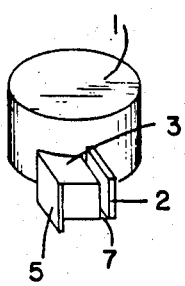
FIG. 2 is a perspective view of an osteoguide showing the guide slot and planar tab means.

FIG. 2 shows a perspective view of the degree block showing the short straight tab 5 that extends below the level of both the degree block and the bottom of the cylinder for several millimeters.

Figure 3:
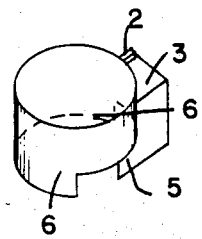
FIG. 3 is a perspective view of an osteoguide showing the curved tab means.

FIG. 3 is an additional perspective view that shows a long curved tab 6 that extends along an arc of the cylinder below the bottom of the cylinder. The long curved tab 6 is longer in longitudinal dimension than the short straight tab 5 coming off the degree block as can be seen in FIG. 4.

Figure 4:
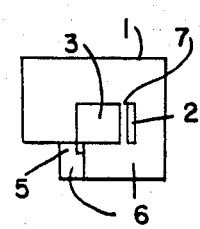
FIG. 4 is a side elevational view showing the relative positions of the tab means.

FIG. 4 is a planar cross sectional view of the wedge guide showing the long curved tab 6, short straight tab 5, degree block portions 2 and 3, slot 7 and cylinder 1 in their relative positions. The long curved tab 6 has an arc less than the width of the crescentic blade to which it's cylinder is matched in circumference; thus, it will be readily apparent that the long curved tab can therefore fit into the osteotomy cut of the crescentic blade it corresponds to. The crescentic blades now available to the practicioner are approximately 18 mm, 15 mm, 10 mm, 9 mm, and 8 mm in width from one end of the arc to the opposite end of the arc. The osteotomy cut is made by the oscillation of this blade against the bone, there is therefore a certain amount of travel so that the cut itself is several millimeters larger (longer) than the respective blade.

Figure 5:
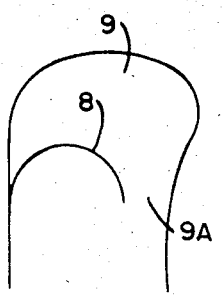
FIG. 5 shows a dorsal view of a crescentic cut in bone.

The bone 9 is cut from one side into and usually beyond the central axis of the bone as depicted in FIG. 5.

Figure 6:
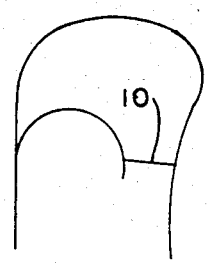
FIG. 6 shows a planar cut in relation to the curved cut of FIG. 5 from a dorsal view.
Figure 7:
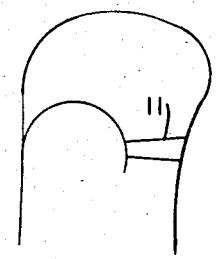
FIG. 7 shows a second planar cut in relation to the first planar cut of FIG. 6 from a dorsal view.
Figure 8:
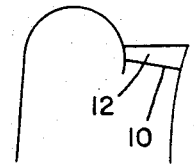
FIG. 8 shows the wedge of bone obtained from the cuts of FIGS. 5–7 from a dorsal view.

The crescentic cut 8 goes all the way through the bone. The bone remains in one piece due to the lack of severence of the opposite side 9A of bone from where the crescentic cut was made. The wedge guide of specific degrees, that corresponds to the crescentic blade used for the osteotomy cut is selected and the long curved tab 6 thereof is placed within the curved slot in the bone as made by the crescentic blade. Then the wedge guide is rotated toward the internal end of the crescentic cut until it can be turned no further; in this illustration clockwise. At this point slot 7 of the guide is near the internal end of the crescentic cut. Utilizing an oscillating or sagittal planar saw, the first planar cut in the bone is made by placing the blade within slot 7 of the guide. This cut 10, shown in FIG. 6, is made half way through the bone. The guide cylinder 1 with its long curved tab 6 within the crescentic cut is now turned in the opposite direction from the internal end of the crescentic cut until the short straight tab 5 fits over the partial first straight cut 10 made by the planar blade. The short straight tab 5 is now pressed down into this first straight partial cut. The short straight tab 5 is a precise number of degrees away from the slot 7. A third cut 11, FIG. 7, which is the second straight cut will be made this number of degrees away from the first planar cut. This third cut 11 which is the second straight cut is made all the way through the bone. The wedge guide can now be removed from the osteotomy site and the first straight cut 10 can be completed through the bone, (FIG. 8), thus yielding the precise wedge 12. The bony parts can now be rotated until the ledges formed by the planar cuts are opposed in the corrected position.

Figure 9:
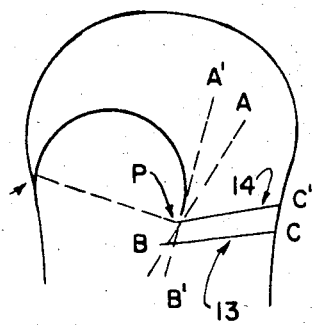
FIG. 9 shows in schematic form how the wedge is obtained by the first and second planar cuts.

FIG. 1A depicts a wedge guide with a slot means 7 at less than 90° to a tangent of the cylinder at its intersection with the cylinder. An example of an osteotomy with this slot means can be seen in FIG. 9. FIG. 9 shows the first planar cut 13 with an angle ABC less than 90°. It further shows a precise wedge made from the second planar cut formed by acute and equal angle A'B'C'.

A line MP, FIG. 9, drawn through the ends of the crescentic cut is not perpendicular to the long axis of the bone and therefore allows the planar cuts 13 and 14 to be within a more advantageous position. If points M and P were at a perpendicular to the long axis of bone the acute planar cuts would travel up through the articular surfaces which would be undesirable.

The acute planar cut in combination with the crescentic cut forms not only the precise wedge but a novel "curved-vee" osteotomy that establishes a moment of force around the curvature into the apex of the Vee, which gives great stability and some natural fixation.

Figure 4A:
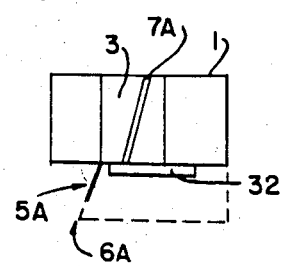
FIG. 4A depicts an embodiment having a slanted slot and planar tab means.
Figure 4B:
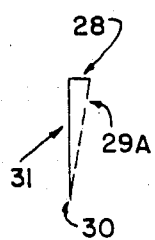
FIG. 4B shows the slanted cut respective to the internal end of the curved cut.
Figure 4C:
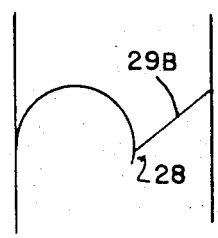
FIG. 4C shows the end of the planar cut internal to the end of the curved cut from a dorsal view.

In FIG. 4A a less than vertical slot means 7A is a precise number of degrees away from an identically slanted straight tab means 5A. To allow for the straight planar cut to meet the crescentic cut along a slanted course the curved tab means must have a slant or an elongation 6A at its periphery that will accomodate the deepest portion of the straight cut. In FIG. 4C, section 28, of the crescentic cut shows the dorsal junction of the planar cut leaving section 28 as a lead for the slanted cut 29A shown in FIG. 4B. Slanted cut 29A reaches the bottom end of crescentic cut 31 at point 30, (FIG. 4B).

Figure 10:
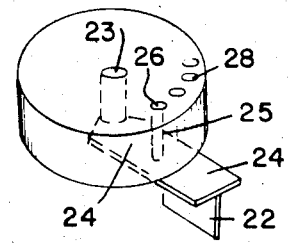
FIG. 10 shows a perspective view of an adjustable planar tab osteoguide.

FIG. 10 shows a perspective view of an adjustable osteoguide that is capable of moving tab element 22 in a multiple number of degrees relative to the slot means. Section 23 shows a central axis on which tab platform 24 can be rotated and affixed by rod 25 and screw 26 through a multitude of holes 28 in the cylinder surface.

Figure 11:
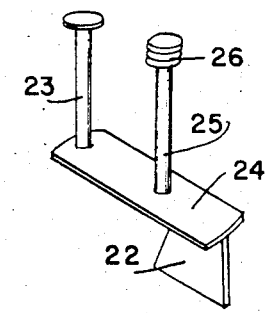
FIG. 11 shows the pin screw mechanism for the moveable tab.

FIG. 11 shows the screw and rod mechanism inserted into platform 24.

Figure 12:
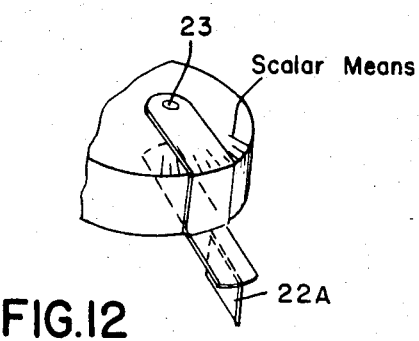
FIG. 12 shows an additional embodiment of adjustment means for a movable tab.
Figure 13:
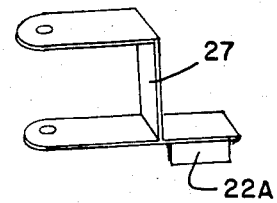
FIG. 13 shows the clip mechanism that holds the planar tab of the FIG. 12 embodiment.

FIG. 12 is another additional embodiment of an adjustable osteoguide having a clear plastic guide clip 27 that can be adjustably rotated a precise numbers of degrees around the cylinder. FIG. 13 is an isolated view of the clip 27 per se.

Figure 14:
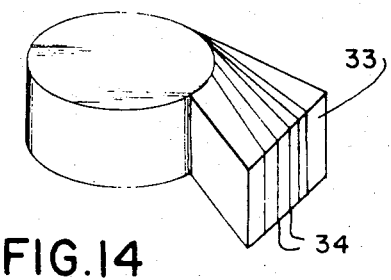
FIG. 14 is a perspective view of another additional embodiment of an adjustable osteoguide that has multiple slot means.

FIG. 14 shows a degree block 33 with multiple slots 34 that are used in the one instance by a removable straight tab means for locking the first planar cut prior to making the second cut through any of the other slots 34 which are precise numbers of degrees from each other.

From the foregoing description, one skilled in the art can easily ascertain the essential characteristics of this invention and without departing from the spirit and scope thereof can make various changes and modifications of the invention to adopt to its various surgical uses.

I claim:

1. An osteotomy method comprising the steps of making a crecentric cut through one side of a bone, making a planar cut through the side of a bone opposite the side with the crecentric cut and extending the planar cut from the crecentric cut to the second side of the bone at an acute angle to a tangent to the convex side of the crecentric cut at an intersection of the crecentric cut and planar cut, forming a second planar cut spaced from the first planar cut and extending the second planar cut from the crecentric cut to the second side of the bone thereby forming a wedge at an acute angle to the convex side of the crecentric cut, removing the wedge and repositioning bone portions to adjoin the first and second planar cut areas and immobilizing and permitting the bone to heal.

2. The method of claim 1 wherein the first and second planar cuts are made parallel to an axis of the crecentric cut.

3. The method of claim 1 wherein the first and second planar cuts are made at an angle relative to an axis of the crecentric cut.

4. The method of claim 1 further comprising inserting a crecentric curvilinear edge in the crecentric cut and guiding a planar saw along a tab extending angularly with respect to the curvilinear crecentric edge.

5. The method of claim 1 further comprising inserting a tab into the first planar cut and guiding a planar saw along the tab through the second planar cut spaced from the first planar cut.

6. A surgical method for changing the axial alignment of a bone, having a longitudinal axis, by severing said bone and repositioning the resulting segments thereof with respect to each other, which method includes the following steps:
   cutting across a portion of said bone in an arcuate cut extending from and through one side of said bone and terminating between said side and the opposed side of said bone, the arc of said arcuate cut being a portion of a circle which has its center offset from said longitudinal axis;
   cutting first and second non-radially extending, circumferentially spaced cuts extending from said arcuate cut toward the opposed side of said bone to form a wedge;
   removing said wedge; and
   rotating the severed bone segments about said arcuate cut to effect said repositioning.

7. The surgical method as set forth in claim 6, wherein said first non-radially extending cut is made near the end of the arcuate cut and the second non-radially extending cut is made from an intermediate point between the ends of said arcuate cut.

8. The surgical method as set forth in claim 6, wherein said first non-radially extending cut is made from an intermediate point between the ends of said arcuate cut and the second non-radially extending cut is made near the end of the arcuate cut.

9. The surgical method as set forth in claim 6, including the further step of using a guide structure for permitting precision determination as to where the respective cuts are to be made in the bone.

* * * * *